US008372834B2

(12) United States Patent
Bremner et al.

(10) Patent No.: US 8,372,834 B2
(45) Date of Patent: Feb. 12, 2013

(54) COMPOSITIONS AND METHODS FOR DELIVERY OF ANTI-CANCER AGENTS

(75) Inventors: John Barnard Bremner, Balgownie (AU); Philip Clingan, Barrack Point (AU); Julie Myree Locke, Woonona (AU)

(73) Assignee: University of Wollongong, Wollongong NSW (AU)

(*) Notice: Subject to any disclaimer, the term of this patent is extended or adjusted under 35 U.S.C. 154(b) by 403 days.

(21) Appl. No.: 12/529,635

(22) PCT Filed: Feb. 29, 2008

(86) PCT No.: PCT/AU2008/000276
§ 371 (c)(1),
(2), (4) Date: Oct. 15, 2009

(87) PCT Pub. No.: WO2008/106721
PCT Pub. Date: Sep. 12, 2008

(65) Prior Publication Data
US 2010/0063057 A1    Mar. 11, 2010

Related U.S. Application Data

(60) Provisional application No. 60/904,363, filed on Mar. 2, 2007.

(51) Int. Cl.
*A61K 31/50* (2006.01)
*A61K 31/495* (2006.01)
*A01N 43/54* (2006.01)
(52) U.S. Cl. .................... 514/247; 514/250; 514/275
(58) Field of Classification Search .................. 514/247, 514/250, 275
See application file for complete search history.

(56) References Cited

U.S. PATENT DOCUMENTS

| | | | |
|---|---|---|---|
| 5,134,127 A | 7/1992 | Stella et al. |
| 5,324,718 A | 6/1994 | Loftsson |
| 5,376,645 A | 12/1994 | Stella et al. |
| 5,427,954 A | 6/1995 | Sandy et al. |
| 5,455,236 A | 10/1995 | Müller et al. |
| 5,534,519 A | 7/1996 | Spears et al. |
| 5,919,816 A | 7/1999 | Hausheer et al. |
| 6,025,488 A | 2/2000 | Hausheer |
| 6,048,844 A | 4/2000 | Falk et al. |
| 6,403,569 B1 | 6/2002 | Achterrath |
| 6,537,988 B2 | 3/2003 | Lee |
| 6,602,870 B2 | 8/2003 | Chazard |
| 6,620,816 B2 | 9/2003 | Winer et al. |
| 6,794,370 B2 | 9/2004 | Achterrath |
| 7,038,071 B2 | 5/2006 | Lal |
| 2001/0034333 A1 | 10/2001 | Kosak |
| 2002/0045632 A1 | 4/2002 | Chazard |
| 2002/0111329 A1 | 8/2002 | Achterrath |
| 2002/0187956 A1 | 12/2002 | Winer et al. |
| 2004/0033271 A1 | 2/2004 | Lederman |
| 2004/0092585 A1 | 5/2004 | Lal |
| 2004/0220135 A1 | 11/2004 | Gray |
| 2004/0229841 A1 | 11/2004 | Achterrath |
| 2004/0229937 A1 | 11/2004 | Dumas et al. |
| 2005/0065169 A1 | 3/2005 | Wang et al. |

FOREIGN PATENT DOCUMENTS

| | | |
|---|---|---|
| CN | 1733312 A | 1/2006 |
| DE | 103 14 377 A1 | 10/2004 |
| EP | 0 427 078 A1 | 5/1991 |
| EP | 1 369 116 A1 | 12/2003 |
| WO | WO 2005/097086 A2 | 10/2005 |

OTHER PUBLICATIONS

Ardalan, L. et al. 1991 "A Phase II Study of Weekly 24-Hour Infusion With High-Dose Fluorouracil With Leucovorin in Colorectal Carcinoma" *Journal of Clinical* Oncology 9(4): 625-630.
Bilensoy, E. et al. 2007 "Thermosensitive mucoadhesive gel formulation loaded with 5-Fu:cyclodextrin complex for HPV-induced cervical cancer" *Journal Incl Phenom Macrocycl Chem* 57:363-370.
Hamilton, S. "Chemotherapy Drugs" [online] Feb. 23, 2006 (date obtained from http://web.archive.org) [retrieved Apr. 4, 2007]. Retrieved from http://www.chemocare.com/bio/folinic_acid.asp.
Supplementary European Search Report for EP 08714327 dated Feb. 23, 2010.
Erlichman, C. et al. 1988 "A randomized trial of fluorouracil and folinic acid in patients with metastatic colorectal carcinoma" *J Clin Oncology* 6: 469-475.
Wolmark, N. et al. 1993 "The Benefit of Leucovorin-Modulated Fluorouracil as Postoperative Adjuvant Therapy for Primary Colon Cancer: Results From National Surgical Adjuvant Breast and Bowel Protocol C-03" *J Clin Oncology* 11: 1879-1887.

*Primary Examiner* — Renee Claytor
(74) *Attorney, Agent, or Firm* — Knobbe Martens Olson & Bear LLP (57) ABSTRACT

The present invention relates to compositions comprising 5-fluorouracil, or a pharmaceutically acceptable salt or analogue thereof, folinic acid, or a pharmaceutically acceptable salt thereof and a cyclodextrin, or a pharmaceutically acceptable salt or derivative thereof. The invention also relates to methods for the treatment of cancer using such compositions.

20 Claims, 6 Drawing Sheets

COMPOSITIONS AND METHODS FOR DELIVERY OF ANTI-CANCER AGENTS

RELATED APPLICATIONS

This application is a U.S. National Phase of International Application No.: PCT/AU2008/000276, filed Feb. 29, 2008, designating the U.S. and published in English on Sep. 12, 2008 as WO 2008/106721, which claims the benefit of U.S. Provisional Application No. 60/904,363, filed Mar. 2, 2007.

TECHNICAL FIELD

The present invention relates to pharmaceutical compositions for the treatment of cancer. In particular, the present invention relates to compositions comprising 5-fluorouracil, cyclodextrin and folinic acid and their use in the treatment of cancer.

BACKGROUND OF THE INVENTION

Chemotherapy plays a key role in the treatment of a range of cancers including colo-rectal, breast and liver cancer. One drug frequently used in chemotherapy is 5-fluorouracil (5-FU) which is known to be a particularly potent anti-cancer agent. While 5-FU can be used independently in chemotherapeutic applications, typically the drug is used in combination with folinic acid as its calcium salt (leucovorin) (D. B. Longley, D. P. Harkin, and P. G. Johnston, "5-Fluorouracil: mechanisms of action and clinical strategies", *Nature Reviews: Cancer*, Vol. 3, 330-338, 2003). The presence of folinic acid synergises the effect of 5-FU by specifically enhancing the capacity of 5-FU to inhibit thymidylate synthase.

In clinical use, the administration of 5-FU and folinic acid to a patient is performed in two separate injections and the optimal synergistic effect of the combination is not realised. Typically, an injectable solution of 5-FU is delivered intravenously at a pH of 9 which results in severe and painful vein damage (phlebitis) in the patient. Consequently a central line is typically used for delivery of 5-FU and this is a significant disadvantage of the present administration technique. Where 5-FU is formulated into a cream for topical use in the treatment of skin cancer, extensive inflammation and pain has been found to occur.

As such, there is a need for improvements in both the delivery of 5-FU and the combination anti-cancer therapy using 5-FU and folinic acid.

Compositions containing both 5-FU and folinic acid have been prepared at more physiologically acceptable pH levels. However these compositions have been shown to be unacceptable owing to the tendency of 5-FU to precipitate out of solution when a clinically appropriate concentration of 5-FU is used. Accordingly there is a need for a composition in which 5-FU and folinic acid can be co-administered at a physiologically acceptable pH at concentrations that are appropriate for clinical use.

The present inventors have surprisingly found that in the presence of a cyclodextrin derivative, a homogeneous solution of 5-FU and folinic acid can be prepared at a physiological pH which minimises harmful side effects.

SUMMARY OF THE INVENTION

In a first aspect, the present invention provides a composition comprising:
(i) 5-fluorouracil (5-FU), or a pharmaceutically acceptable salt or analogue thereof;
(ii) folinic acid (FA), or a pharmaceutically acceptable salt thereof; and
(iii) a cyclodextrin or a pharmaceutically acceptable salt or derivative thereof.

The cyclodextrin (CD) or salt or derivative thereof may be present in a concentration sufficient to prevent the 5-FU or salt or analogue thereof from precipitating out of solution. The pH of the composition may be about 5 to about 9, or about 6.5 to about 8 or about 7.0 to about 7.8. The cyclodextrin or salt or derivative thereof may be present at a concentration of between about 0.1 and about 30% or between about 1 and is about 30% on a w/v basis, or between about 1 and about 300 mg/ml or between about 10 and about 300 mg/ml. The 5-FU or salt or analogue thereof may be present at a concentration of between about 1 and about 50 mg/ml or between about 5 and about 50 mg/ml. The folinic acid or salt thereof may be present at a concentration of between about 0.1 and about 25 mg/ml or between about 0.1 and about 15 mg/ml or between about 0.1 and about 12 mg/ml.

The composition may be a composition for the treatment and/or prevention of cancer.

The 5-FU and cyclodextrin may be present in the composition in the form of a non-covalent complex, i.e. the 5-FU may be complexed to the cyclodextrin but not covalently bound thereto.

The folinic acid and cyclodextrin may be present in the composition in the form of a non-covalent complex, i.e. the folinic acid may be complexed to the cyclodextrin but not covalently bound thereto.

The composition may comprise one or more pharmaceutically acceptable carrier, diluent and/or adjuvant. The carrier may be an aqueous carrier, e.g. saline solution. The composition may be an aqueous composition.

The analogue of 5-FU may be for example 5-fluoro-2-deoxyuridine (5-FUdr).

The composition may be in the form of a solution, e.g. an aqueous solution. Each of the components (i, ii, iii above) may be in solution in the composition. The composition may contain no solid matter. Thus each of the components (i, ii, iii above) may be completely in solution in the composition.

The composition may be a synergistic composition.

The pharmaceutically acceptable salt of folinic acid may be calcium folinate (leucovorin) or sodium folinate. The salt may be in the form of a hydrate, for example calcium folinate pentahydrate.

The folinic acid, or pharmaceutically acceptable salt thereof, may be present in either of its enantiomeric forms, or as a racemic mixture. It may be the 6(S) diastereomer or the 6(R) diastereomer (wherein the glutamic acid residue of the folinic acid or folinate is in the L form), or it may be a mixture of these in any desired ratio, such as about 1:1 or some other ratio. It may be a mixture of these in which the 6(S) isomer is enriched. It may be between about 51 and about 100% enriched, or between about 55 and 99%, 55 and 95%, 55 and 75%, 55 and 65%, 75 and 85%, 75 and 95%, 85 and 95% or 75 and 99% enriched, e.g. about 51, 52, 53, 54, 55, 60, 65, 70, 75, 80, 85, 90, 95, 96, 97, 98, 99 or 100% enriched. It should be noted that the 6(S) form having the glutamic acid residue in the L form is pharmaceutically active.

The cyclodextrin may be α-cyclodextrin, γ-cyclodextrin, or a derivative or salt thereof, or may be a β-cyclodextrin; or a derivative or salt thereof.

The cyclodextrin may be a cyclodextrin sulfate, or a salt thereof.

In one embodiment, the cyclodextrin is a sulfated sodium salt of β-cyclodextrin, optionally a polysulfated sodium salt or a mixture of sulfated sodium salts with differing degrees of sulfation. In another embodiment, the cyclodextrin is a hydroxyalkyl β-cyclodextrin, for example hydroxypropyl-β-cyclodextrin. Alternatively, the cyclodextrin may be a mixture of different types of cyclodextrins, for example a mixture of hydroxyalkyl β-cyclodextrin and sulfated β-cyclodextrin.

In another embodiment there is provided a composition comprising, or consisting of:
(i) 5-fluorouracil (5-FU), or a pharmaceutically acceptable salt or analogue thereof;
(ii) folinic acid, or a pharmaceutically acceptable salt thereof;
(iii) a cyclodextrin or a pharmaceutically acceptable salt or derivative thereof; and
(iv) a pharmaceutically acceptable carrier;
wherein (i), (ii), and (iii) are dissolved in (iv).

The cyclodextrin may be selected from the group consisting of: a hydroxyalkyl β-cyclodextrin and a sulfated β-cyclodextrin, or a combination thereof. The hydroxyalkyl β-cyclodextrin may be hydroxypropyl-β-cyclodextrin, or more specifically 2-hydroxypropyl-β-cyclodextrin.

In another embodiment there is provided a composition comprising, or consisting of:
(i) 5-fluorouracil (5-FU), or a pharmaceutically acceptable salt or analogue thereof in a concentration of between about 1 and about 50 mg/ml;
(ii) folinic acid, or a pharmaceutically acceptable salt thereof, in a concentration of between about 0.1 and about 5 mg/ml;
(iii) a cyclodextrin or a pharmaceutically acceptable salt or derivative thereof in a concentration of between about 10 and about 300 mg/ml; and
(iv) a pharmaceutically acceptable carrier;
wherein (i), (ii), and (iii) are dissolved in (iv).

In another embodiment there is provided a composition comprising, or consisting of:
(i) 5-fluorouracil (5-FU), or a pharmaceutically acceptable salt or analogue thereof in a concentration of between about 10 and about 20 mg/ml;
(ii) folinic acid, or a pharmaceutically acceptable salt thereof, in a concentration of between about 0.5 and about 2 mg/ml;
(iii) a cyclodextrin or a pharmaceutically acceptable salt or derivative thereof in a concentration of between about 20 and about 200 mg/ml; and
(iv) a pharmaceutically acceptable carrier;
wherein (i), (ii), and (iii) are dissolved in (iv).

The cyclodextrin may be selected from the group consisting of: a hydroxyalkyl β-cyclodextrin and a sulfated β-cyclodextrin, or a combination thereof. The hydroxyalkyl β-cyclodextrin may be hydroxypropyl-β-cyclodextrin.

The pharmaceutically acceptable carrier may be saline solution.

In another embodiment there is provided a composition comprising, or consisting of:
(i) 5-fluorouracil (5-FU) at a concentration of about 15 mg/ml;
(ii) folinic acid calcium salt at a concentration of about 1 mg/ml;
(iii) β-cyclodextrin sulfate salt at a concentration of about 45 mg/ml; and
(iv) a pharmaceutically acceptable carrier;
wherein (i), (ii), and (iii) are dissolved in (iv).

In another embodiment there is provided a composition comprising, or consisting of:
(i) 5-fluorouracil (5-FU) at a concentration of about 15 mg/ml;
(ii) folinic acid calcium salt at a concentration of about 1 mg/ml;
(iii) β-cyclodextrin sulfate salt at a concentration of about 175 mg/ml; and
(iv) a pharmaceutically acceptable carrier;
wherein (i), (ii), and (iii) are dissolved in (iv).

In another embodiment there is provided a composition comprising, or consisting of:
(i) 5-fluorouracil (5-FU) at a concentration of about 45 mg/ml;
(ii) folinic acid calcium salt at a concentration of about 1 mg/ml;
(iii) β-cyclodextrin sulfate salt at a concentration of about 45 mg/ml; and
(iv) a pharmaceutically acceptable carrier;
wherein (i), (ii), and (iii) are dissolved in (iv).

The β-cyclodextrin sulfate salt may comprise between 6 and 14 sulfate groups. The pharmaceutically acceptable carrier may be 0.9% saline solution.

The β-cyclodextrin sulfate salt may be a sodium salt.

In another embodiment there is provided a composition comprising, or consisting of:
(i) 5-fluorouracil (5-FU) at a concentration of about 15 mg/ml;
(ii) folinic acid calcium salt at a concentration of about 1 mg/ml;
(iii) 2-hydroxypropyl-β-cyclodextrin at a concentration of about 100 mg/mL; and
(iv) a pharmaceutically acceptable carrier;
wherein (i), (ii) and (iii) are dissolved in (iv).

The pharmaceutically acceptable carrier may be 0.9% saline solution.

In another embodiment there is provided a composition comprising, or consisting of:
(i) 5-fluorouracil (5-FU) at a concentration of about 15 mg/ml;
(ii) folinic acid calcium salt at a concentration of about 1 mg/ml;
(iii) heptakis(6-O-sulfo)-β-cyclodextrin salt at a concentration of about 50 mg/mL; and
(iv) a pharmaceutically acceptable carrier;
wherein (i), (ii) and (iii) are dissolved in (iv):

The pharmaceutically acceptable carrier may be 0.9% saline solution.

The heptakis(6-O-sulfo)-β-cyclodextrin salt may be a sodium salt.

In a second aspect of the invention there is provided a process for making a composition, comprising combining:
(i) 5-fluorouracil (5-FU), or a pharmaceutically acceptable salt or analogue thereof;
(ii) folinic acid, or a pharmaceutically acceptable salt thereof; and
(iii) a cyclodextrin or a pharmaceutically acceptable salt or derivative thereof.

The concentrations and identities of the components may be as described above in the first aspect of this invention. The process may comprise combining (i) with (iii), and then adding (ii). When adding (ii), it may be in solution, optionally in aqueous solution. The process may also comprise sterilising the composition. The sterilising may comprise filtration (e.g. microfiltration), UV radiation, gamma radiation, some other form of sterilising radiation or some other form of sterilising. The sterilising may be conducted so as not to damage or degrade any of components (i) to (iii) above. Thus sterilising radiation (UV, gamma or other), if used, should be in a dose sufficiently high to sterilise the composition but sufficiently low to avoid damage or degradation of the components specified.

The composition may be a composition for the prevention and/or treatment of cancer.

In an embodiment, (i) and (iii) are combined in the presence of a carrier, optionally an aqueous carrier, to form a mixture, and (ii) is added to the mixture. The mixture may be a solution, optionally an aqueous solution. The carrier may be a solvent, optionally an aqueous solvent e.g. saline solution. (i) and (iii) may, independently, be partially soluble in the carrier, optionally sparingly soluble. Following combination of (i) and (iii) in the presence of the carrier to form a mixture, the mixture may be agitated to at least partially dissolve (i) and (iii) in the carrier. The dissolution may comprise formation of a non-covalent complex between (i) and (iii). The agitation may comprise stirring, swirling, shaking, sonicating or a combination of two or more thereof. The agitation may be conducted at elevated temperature, e.g. between about 30 and about 60° C. The composition may be agitated following addition of (ii). The agitation may be as described above.

In another embodiment there is provided a process for making a composition, comprising:
  combining 5-fluorouracil (5-FU), or a pharmaceutically acceptable salt or analogue thereof, and a cyclodextrin or a pharmaceutically acceptable salt or derivative thereof in the presence of an aqueous solvent to form a mixture;
  optionally agitating, and optionally heating, the mixture to form a solution; and
  adding an aqueous solution of folinic acid, or a pharmaceutically acceptable salt thereof, to the solution to form the composition.

The step of adding the aqueous solution may be conducted so as to form a composition in which the 5-FU or salt or analogue thereof, the cyclodextrin or salt or derivative thereof and the folinic acid or salt thereof are all in solution in the composition, optionally such that no solid matter is present the composition. The composition may be optionally agitated, and optionally heated, following the step of adding the aqueous solution. The agitation of the composition may be sufficient to render the composition homogeneous or to ensure that all of the components of the composition are completely in solution.

In another embodiment there is provided a process for making a composition, comprising:
  combining 5-fluorouracil (5-FU), or a pharmaceutically acceptable salt or analogue thereof, and a cyclodextrin or a pharmaceutically acceptable salt or derivative thereof in the presence of an aqueous solvent to form a mixture;
  optionally agitating, and optionally heating, the mixture to form a solution;
  adding an aqueous solution of folinic acid, or of a pharmaceutically acceptable salt thereof, to the solution to form the composition;
  agitating, and optionally heating, the composition sufficient to ensure that all components are in solution; and
  sterilising the composition.

In another embodiment there is provided a process for making a composition, comprising:
  combining 5-fluorouracil (5-FU), or a pharmaceutically acceptable salt or analogue thereof, in an amount of between about 5 and about 50 mg per ml of final composition, and a cyclodextrin or a pharmaceutically acceptable salt or derivative thereof in an amount of between about 20 and about 200 mg per ml of final composition in the presence of an aqueous solvent to form a mixture;
  optionally agitating, and optionally heating, the mixture to form a solution;
  adding an aqueous solution of folinic acid, or of a pharmaceutically acceptable salt thereof, at a concentration of between about 5 and 20 mg/ml and in an amount of between about 50 and about 200 µL per ml of final composition, to the solution to form the composition;
  agitating, and optionally heating, the composition sufficient to ensure that all components are in solution; and
  sterilising the composition.

In a third aspect, the present invention provides a method for the treatment or prevention of cancer in a patient in need of said treatment or prevention, said method comprising administration of a therapeutically effective amount of the composition of the first aspect.

In a fourth aspect, the present invention provides a method for inhibiting the proliferation of cancer cells, said method comprising exposing the cancer cells to the composition of the first aspect.

The cancer or cancer cells may be primary or secondary and may include one or more of the following: prostate cancer, lung cancer (for example non-small cell lung cancer), colo-rectal cancer (which is to be understood to encompass colon cancer and bowel cancer), cervical cancer, breast cancer, ovarian cancer, gastric cancer, primary hepatoma, skin cancer, pancreatic cancer, cholangiocarcinoma or a cancer of the head or neck, and cancer cells therefrom.

The skin cancer may be non-melanoma skin cancer.

The patient may be a mammal, for example a human.

Definitions

In the context of this specification, the term "comprising" means "including principally, but not necessarily solely". Furthermore, variations of the word "comprising", such as "comprise" and "comprises", have correspondingly varied meanings.

As used herein, the term "synergistic" refers to a greater than additive effect that is produced by a combination of folinic acid and 5-FU, which exceeds the effect that would otherwise result from use of the 5-FU and folinic acid alone.

A "therapeutically effective amount", as used herein, includes within its meaning a non-toxic but sufficient amount of 5-FU and folinic acid to provide the desired therapeutic effect. The exact amount required will vary from subject to subject depending on factors such as the subject's general health, the subject's age, the subject's gender and the stage and severity of the cancer.

As used herein, the term "prevention" includes either preventing the onset of clinically evident cancer altogether, or delaying its onset.

As used herein, the term "treatment" includes partial or total inhibition of cancer growth, as well as partial or total destruction of the cancer cells.

As used herein the term "complex" is understood to mean a non-covalent physical interaction between two or more chemical entities.

As used herein, the term "fluorodex" (abbreviation FD) is understood to mean a composition containing 5-FU and folinic acid salt together with a cyclodextrin or derivative thereof in aqueous solution, as disclosed in the present invention.

BRIEF DESCRIPTION OF THE FIGURES

A preferred embodiment of the present invention will now be described, by way of example only, with reference to the accompanying drawings wherein.

DETAILED DESCRIPTION OF THE INVENTION

Compositions and Methods of Preparation

The present invention relates to compositions comprising 5-FU, or a pharmaceutically acceptable salt or analogue thereof, folinic acid, or a pharmaceutically acceptable salt thereof, and a cyclodextrin, or a pharmaceutically acceptable salt or derivative thereof, which prevents 5-FU from precipitating out of solution at a pH of about 5 to about 9. The invention also contemplates use of the compositions for the treatment of cancer.

In the present context, an analogue of 5-FU is a compound having comparable or similar pharmacological activity, particularly in a human patient, to 5-FU, and similar solubility/complexation properties, so that in a composition according to the present invention, when made with the analogue, the analogue remains in solution. In the present specification, reference to 5-FU will be taken to include a corresponding reference to a pharmaceutically acceptable salt or analogue thereof, reference to folinic acid will be taken to include a corresponding reference to a pharmaceutically acceptable salt or derivative thereof, and reference to cyclodextrin will be taken to include a corresponding reference to a pharmaceutically acceptable salt or derivative thereof, unless the contrary is indicated or implied.

The use of the compositions of the invention provide the following advantages over current methods of cancer treatment using 5-FU and folinic acid:

(i) improving the delivery of both 5-FU and folinic acid by allowing simultaneous administration of the two compounds;

(ii) minimisation of side effects that are prevalent when 5-FU is administered at higher pH values of about 9;

(iii) reduction in administration time and costs (in the clinic) by enabling the combination of an anticancer agent and its biomodulator to be administered in a single dose;

(iv) lower pH means that a central line usually required to prevent phlebitis may not be required, therefore significantly simplifying administration; and (v) possibly reduced stress on the patient.

In the compositions of the present invention, cyclodextrin and 5-FU may form a complex in solution. This complex may be a "host-guest" or "inclusion complex". The complex may result in the otherwise insoluble 5-FU being soluble in aqueous solution at pH values of between about 5 to about 8. Alternatively, the cyclodextrin and 5-FU may be associated through some other form of non-covalent interaction. Cyclodextrin and folinic acid may also form a complex in solution. This complex may be a "host-guest" or "inclusion complex".

The 5-FU present in the compositions of the invention may be present as a pharmaceutically acceptable salt. By "pharmaceutically acceptable salt" it is meant those salts of 5-FU which are suitable for use in contact with the tissues of humans and other animals without undue toxicity, irritation, allergic response and the like, and are commensurate with a reasonable benefit/risk ratio. Pharmaceutically acceptable salts are well known in the art.

For instance, suitable pharmaceutically acceptable salts of 5-FU include the sodium salt, which may be obtained from reaction with sodium hydroxide.

The folinic acid present in the composition may be present as a salt of an alkali metal (e.g. sodium, potassium) or a salt of an alkaline earth metal (e.g. magnesium, calcium). In one embodiment, the folinic acid may be present as calcium folinate.

Cyclodextrins suitable for use in accordance with the present invention include natural and chemically modified cyclodextrins. The cyclodextrin may be an α-cyclodextrin, a β-cyclodextrin, a γ-cyclodextrin, or a derivative or pharmaceutically acceptable salt thereof. Mixtures of any two or more of the above cyclodextrins are also contemplated in the compositions of the invention.

Derivatives of cyclodextrins that may be used in the compositions may include cyclodextrins whereby one, or some, or all of the hydroxy groups are converted to other functional groups. As a result, the degree of substitution of the cyclodextrin may vary.

In one embodiment, one or more of the hydroxy groups may be converted to OR groups. R may be a hydrocarbon group having between 1 and 20 carbon atoms, or between 1 and 15, or between 1 and 10, or between 1 and 9, or between 1 and 8, or between 1 and 7, or between 1 and 6, or between 1 and 5, or between 1 and 4 carbon atoms, for example methyl, allyl, ethyl, propyl, isopropyl, propargyl, butyl, but-2-enyl, secbutyl, pentyl, 3-methyl-pent-2-enyl, hexyl, heptyl, octyl, nonyl, decyl etc. In one embodiment, the hydrocarbon group is a branched or straight chain alkyl group. The hydrocarbon group may be optionally substituted with one or more halo groups and/or one or more hydroxy groups, such that R is a halo-substituted hydrocarbon or a hydroxy-substituted hydrocarbon, for example a hydroxyalkyl group. Examples of hydroxyalkyl groups include, but are not limited to —$CH_2CH(OH)CH_3$, —$CH_2CH_2OH$, —$CH_2CH_2CH_2(OH)CH_3$, —$CH(OH)CH_2CH_3$ and —$CH(OH)CH_2CH_2CH_2CH_3$. In one embodiment, the cyclodextrin is a hydroxyalkyl β-cyclodextrin, for example hydroxypropyl-β-cyclodextrin.

Derivatives of cyclodextrins also include anionic cyclodextrins such as carboxymethyl cyclodextrins, cyclodextrin sulfates, cyclodextrin sulfonates, cyclodextrin phenolates and cyclodextrin phosphates, or mixtures thereof. In one embodiment, the cyclodextrin derivative may be a sulfated α-, β-, or γ-cyclodextrin, or a salt thereof, for example a sodium salt. The sulfated cyclodextrin may be polysulfated or comprise a mixture of sulfate and hydroxy groups. In one embodiment, the sulfated cyclodextrin is a β-cyclodextrin comprising between 3 and 20, or between 3 and 18, or between 4 and 16, is or between 4 and 14, or between 5 and 13, or between 5 and 12, or between 5 and 11, or between 6 and 10, or between 7 and 9, or between 9 and 12, or between 5 and 10 sulfate groups. The sulfate groups may be present as salts, for example sodium salts. In one embodiment, the cyclodextrin derivative is heptakis(6-O-sulfo)-β-cyclodextrin, or a salt thereof.

Further cyclodextrin derivatives which may be used include sulfoether cyclodextrins such as sulfoalkylether cyclodextrins, wherein the alkyl group comprises between 1 and 15 carbon atoms, or between 1 and 12, or between 1 and 10, or between 1 and 9, or between 1 and 8, or between 1 and 7, or between 1 and 6, or between 1 and 5, or between 1 and 4 carbon atoms, for example sulfobutyl β-cyclodextrin (Captisol®). The alkyl group may be of the formula —$(CH_2)_n$—, wherein n is a number between 1 and 8, or between 1 and 7, or between 1 and 6, or between 1 and 5 or between 1 and 4.

Additional cyclodextrin derivatives that may be suitable for use in the compositions of the present invention are those disclosed in "Chemical Reviews: Cyclodextrins", V. T. D'Souza and K. B. Lipkowitz, Vol. 98, No. 5 (American Chemical Society, 1998), which is incorporated herein by reference.

As noted above, the degree of substitution of the cyclodextrin may vary. Suitable cyclodextrins therefore include for example those cyclodextrins wherein one, or some, or all of the hydroxy groups are substituted. The degree of substitution may be between about 1 and 20, or between about 5 and 20, 10 and 20, 1 and 10, 1 and 5, 5 and 15, 5 and 10 or 10 and 15, e.g. about 1, 2, 3, 4, 5, 6, 7, 8, 9, 10, 11, 12, 13, 14, 15, 16, 17, 18, 19 or 20. The cyclodextrin may be a mixture of cyclodextrins of different degrees of substitution. In such a case the average degree of substitution may be between about 1 and 20, or between about 5 and 20, 10 and 20, 1 and 10, 1 and 5, 5 and 15, 5 and 10 or 10 and 15, e.g. about 1, 2, 3, 4, 5, 6, 7, 8, 9, 10, 11, 12, 13, 14, 15, 16, 17, 18, 19 or 20. In one embodiment where the cyclodextrin is a hydroxypropyl-β-cyclodextrin, the average degree of substitution may be between about 4 and about 12, or between about 5 and about 10, or between about 5 and about 9, or between about 6 and about 8, or about 7.

Generally the amount of cyclodextrin used in the compositions of the invention is an amount sufficient to ensure that the 5-FU present in the compositions is maintained in solution. The molar ratio of CD:5-FU may be between about 1:10 and about 3:1, or between about 1:10 and 1:1, 1:10 and 1:2, 1:10 and 1:5, 1:5 and 3:1, 1:5 and 1:1, 1:3 and 3:1, 1:8 and 3:1, 1:8 and 2:1, 1:8 and 1:1, 1:8 and 1:2, 1:8 and 1:5, 1:3 and 2:1, 1:3 and 1:1, 1:3 and 1.1:1, 1:3 and 1.2:1, 1:3 and 1.3:1, 1:3 and 1.4:1, 1:3 and 1.5:1, 1:3 and 2:1, is 1:3 and 2.5:1, 1:2.5 and 3:1, 1:2 and 3:1, 1:1.5 and 3:1, 1:1.4 and 3:1, 1:1.3 and 3:1, 1:1.2 and 3:1, 1:1.1 and 3:1, 1:1 and 3:1, 1.5:1 and 3:1, 2:1 and 3:1, 2.5:1 and 3:1, 2:1 and 1:2, 1.5:1 and 1:1.5, 1.4:1 and 1:1.4, 1.3:1 and 1:1.3, 1.2:1 and 1:1.2 or 1.1:1 and 1:1.1, e.g. about 1:10, 1:9, 1:8, 1:7, 1:6, 1:5, 1:4.5, 1:4, 1:3.5, 1:3, 1:2.5, 1:2, 1:1.5, 1:1.4, 1:1.3, 1:1.2, 1:1.1, 1:1, 1.1:1, 1.2:1, 1.3:1, 1.4:1, 1.5:1, 2:1, 2.5:1 or 3:1. This ratio may depend on the particular CD used.

The composition may be mildly or moderately acidic, neutral or mildly or moderately basic. The pH of the composition may be between about 5.0 and about 9.0, or between about 5.0 and about 8.0, or between about 5.0 and about 7.0, or between about 5.5 and about 8.0, or between about 6.0 and about 8.0, or between about 6.5 and about 8.0, or between about 7.0 and about 8.0, or between about 7.5 and about 8.0, or between about 7.0 and about 9.0, or between about 7.5 and 7.8, or between about 7.5 and about 7.7, or between about 7.6 and about 7.7, or between about 6.7 and about 7.7, or between about 6.8 and about 7.6, or between about 7.0 and about 7.6, or between about 7.2 and about 7.6, or between about 7.3 and about 7.6, or between about 7.3 and 7.5. For example the pH may be about 5.0, 5.1, 5.3, 5.5, 5.7, 5.9, 6.1, 6.3, 6.5, 6.7, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9 or 9.0.

In one embodiment, the composition of the invention may be prepared by mixing solid 5-FU (15 mg), saline (0.9%, 0.87 ml), sodium hydroxide solution (0.9M, 30 μL) and a cyclodextrin, (e.g. β-cyclodextrin sulfated sodium salt as a mixture of 9-12 sulfates per cyclodextrin residue: 45 mg). The resulting suspension is sonicated at about 30 to 60° C. until almost all of the 5-FU has dissolved. A solution of folinic acid (for example, calcium folinate (1 mg: 10 mg/mL) in 0.9% saline is then added, and the mixture subjected to sonication at 30 to 60° C. until a homogenous solution is formed. The temperature of the sonication may be between about 30 and 50, 30 and 40, 40 and 60, 40 and 60 or 40 and 50° C., e.g. about 30, 35, 40, 45, 50, 55 or 60° C., or may be above 60° C. or below 30° C.

The homogeneous solution is cooled and allowed to stand at room temperature for about 1 hour. The solution may then be filtered under aseptic conditions and stored at room temperature in the absence of light. The pH of the solution may be between about 7.3 and about 7.5.

In an alternative embodiment, the composition of the invention may be prepared by dissolving a cyclodextrin (e.g. β-cyclodextrin sulfated sodium salt or 2-hydroxypropyl-β-cyclodextrin) in water, and adding a solution of 5-FU (for example 5-fluorouracil Injection BP, 50 mg/mL) and a solution of folinic acid (for example about 200 μL of a 10 mg/mL solution). Thus 300 μL of the above solution may be used per mL of formulation to give a final concentration of 15 mg/mL of 5-FU. The resulting solution is agitated to facilitate mixing. Acid (for example HCl) may then be added if necessary to bring the pH to 7.4±0.1. The solution may then be filtered under aseptic conditions and stored at room temperature in the absence alight.

In a further embodiment it is possible to remove the solvent and dry the composition for resuspension in solution at a later date. Lyophilized formulations have disadvantages with respect to the liquid formulation. The freeze-dried formulation may require extensive sonication and extra preparation by medical staff.

Pharmaceutical Compositions and Methods of Administration

The compositions of the invention are useful in the treatment of cancer in a patient, by administering a therapeutically effective amount of composition to a subject.

Cancers which the compositions and methods of the present invention are particularly useful for treating include primary or secondary cancers for example, prostate cancer, lung cancer (for example non-small cell lung cancer), cervical cancer, breast cancer, ovarian cancer, gastric cancer, upper GI cancers, primary hepatoma, pancreatic cancer, cholangiocarcinoma, colo-rectal cancer (which is to be understood to encompass colon cancer and bowel cancer), pancreatic cancer, head and neck cancer, breast cancer and skin cancer, for example non-melanoma skin cancer.

In a therapeutic application, compositions are administered to a patient already suffering from cancer, in an amount sufficient to cure, or at least partially arrest the cancer and its complications. The compositions should provide a quantity of 5-FU and folinic acid sufficient to effectively treat the cancer.

In general, suitable compositions for use in accordance with the methods of the present invention may be prepared according to methods and procedures that are known to those of ordinary skill in the art, and accordingly may include a pharmaceutically acceptable carrier, diluent and/or adjuvant. The diluents, adjuvants and excipients must be "acceptable" in terms of being compatible with the other components of the composition, and not deleterious to the recipient thereof.

Compositions may be administered by standard routes. In general, the compositions may be administered intravenously, intraperitoneally, intraarterially, or topically. They may also be administered intramuscularly, subcutaneously or transdermally (e.g. by means of a patch). Administration may be systemic, regional or local. The particular route of administration to be used in any given circumstance will depend on a number of factors, including the type of cancer being treated, the severity and extent of the cancer, the required dosage of 5-FU and folinic acid to be delivered and any potential side-effects.

Examples of pharmaceutically acceptable carriers or diluents are demineralised or distilled water, BP or USP water, saline solution, Ringer's solution, glucose solution, vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrrolidone; agar; carrageenan; gum tragacanth or gum acacia, and petroleum jelly. Typically, the carrier or carriers will form from 10% to 99.9% by weight of the compositions.

The compositions of the invention may be in a form suitable for administration by injection, in the form of an ointment, cream or lotion suitable for topical administration, or in a form suitable for administration by injection intravenously, intraperitoneally or intraarterially.

For administration as an injectable solution or suspension, non-toxic parenterally acceptable diluents or carriers can include, Ringer's solution, isotonic saline, glucose solution, distilled water, phosphate buffered saline, ethanol and 1,2 propylene glycol.

Adjuvants typically include emollients, emulsifiers, thickening agents, preservatives, bactericides and buffering agents.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

Topical formulations comprise the composition of the invention together with one or more acceptable carriers, and optionally any other therapeutic ingredients. Formulations suitable for topical administration include liquid or semi-liquid preparations suitable for penetration through the skin to the site of where treatment is required, such as liniments, lotions, creams, ointments or pastes.

Lotions according to the present invention include those suitable for application to the skin. Lotions or liniments for application to the skin may also include an agent to hasten drying and to cool the skin, such as an alcohol or acetone, and/or a moisturiser such as glycerol, or oil such as castor oil or arachis oil.

The compositions may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The therapeutically effective dose level for any particular patient will depend upon a variety of factors including: the cancer being treated and the severity of the cancer, the age, body weight, general health, sex and diet of the patient, the time of administration, the route of administration, the duration of the treatment, drugs used in combination or coincidental with the treatment, together with other related factors well known in medicine.

One skilled in the art would be able, by routine experimentation, to determine an effective, non-toxic amount of agent or compound which would be required to treat applicable diseases and conditions.

Generally, an effective dosage of 5-FU is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours; or about 5.0 to 10.0 mg/kg body weight per 24 hours.

Generally, an effective dosage of folinic acid is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours. It may be a low dose or high dose folinic acid composition.

In a composition according to the present invention the 5-FU and the folinic acid may be present in pharmaceutically effective concentrations. The 5-FU may be present in a concentration of between about 1 and about 50 mg/ml, or between about 1 and 40, 1 and 30, 1 and 20, 1 and 10, 1 and 5, 5 and 50, 10 and 50, 20 and 50, 5 and 30, 5 and 20 or 10 and 20 mg/ml, e.g. about 1, 2, 3, 4, 5, 6, 7, 8, 9, 10, 11, 12, 13, 14, 15, 16, 17, 18, 19, 20, 25, 30, 35, 40, 45 or 50 mg/ml. The folinic acid may be present in a concentration of between about 0.01 and about 25 mg/ml, or between about 0.01 and 25, 0.1 and 20, 0.1 and 15, 0.1 and 10, 0.1 and 5, 0.1 and 2, 0.1 and 1, 1 and 25, 5 and 25, 10 and 25, 15 and 25, 1 and 15, 1 and 10, 1 and 5, 0.5 and 5, 0.5 and 2, 5 and 20, 5 and 10 or 10 and 20 mg/ml, e.g. about 0.1, 0.2, 0.3, 0.4, 0.5, 0.6, 0.7, 0.8, 0.9, 1, 2, 3, 4, 5, 6, 7, 8, 9, 10, 15, or 25 mg/ml. The CD may be present in a concentration of between about 1 and about 300 mg/ml, or between about 1 and 250, 1 and 200, 1 and 150, 1 and 100, 1 and 50, 1 and 20, 1 and 10, 5 and 300, 5 and 250, 5 and 200, 5 and 150, 5 and 100, 5 and 50, 5 and 20, 5 and 10, 10 and 300, 20 and 300, 30 and 300, 40 and 300, 50 and 300, 100 and 300, 200 and 300, 50 and 200, 5 and 100, 45 and 125, 25 and 100, 50 and 100, or 100 and 200 mg/ml, e.g. about 5, 10, 15, 20, 25, 30, 35, 40, 45, 50, 60, 70, 80, 90, 100, 150, 200, 250 or 300 mg/ml.

Typically, in therapeutic applications, the treatment would be for the duration of the cancer.

Further, it will be apparent to one of ordinary skill in the art that the optimal quantity and spacing of individual dosages will be determined by the nature and extent of is the cancer being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per day for a defined number of days, can be ascertained by those skilled in the art using conventional course of treatment determination tests.

Those skilled in the art will appreciate that in accordance with the methods of the present invention the composition may be administered alone or in conjunction with one or more additional agents as part of a combination therapy. For example, the composition of the invention may be administered together with one or more additional compounds capable of decreasing cell proliferation and invasion and increasing apoptosis in cancer.

For such combination therapies, each component of the combination therapy may be administered sequentially in any order, at the same time or at different times, so as to provide the desired effect. When administered separately, it may be preferred for the components to be administered by the same route of administration, although it is not necessary for this to be so.

Combination Regimens

Therapeutic advantages may be realised through combination regimens. In combination therapy the respective agents may be administered simultaneously, or sequentially in any order. Accordingly, methods of treatment according to the present invention may be applied in conjunction with conventional therapy, such as radiotherapy, chemotherapy, surgery, or other forms of medical intervention.

The present invention will now be described with reference to specific examples, which should not be construed as in any way limiting the scope of the invention.

EXAMPLES

Example 1

Preparation of Compositions 1.1 Preparation of a Composition from Solid 5-Fluorouracil (FD2 Method).

Makes 1 mL of composition: 5-FU (15 mg), 0.9% Saline (870 µL), NaOH (30 µL of 0.9 M) and β-cyclodextrin sulfated sodium salt (45 mg) were mixed and the suspension was sonicated at 40-50° C. until almost all of the 5-FU had dissolved. Folinic acid solution (Leucovorin Calcium 10 mg/mL, 100 µL) was added and the mixture was sonicated at 40-50° C. until a homogeneous solution formed. The mixture was cooled and allowed to stand for 1 h at room temperature. The pH of this solution was 7.4±0.1. The solution was filtered under aseptic conditions and stored at room temperature protected from light. This composition is named FD1. Using this method but increasing the concentration of β-cyclodextrin sulfated sodium salt to 175 mg/mL produced a composition named FD2.

1.2 Preparation of a Composition from 5-Fluorouracil Solution (FD4 Method).

Makes 1 mL of composition: β-cyclodextrin sulfated sodium salt (45 mg) was dissolved in water (525 µL). 5-FU solution (5-Fluorouracil Injection BP, 50 mg/mL, 300 µL) and 100 µl of folinic acid solution (Leucovorin Calcium 10 mg/mL) were added to the cyclodextrin solution which was agitated to mix. HCl (75 µL of 1.000M solution) was added to the solution to bring the pH to 7.4±0.1. The solution was filtered under aseptic conditions and stored at room temperature, protected from light. This composition is named FD45c.

1.3 Preparation of a Composition from 5-Fluorouracil Solution (FD4 Method).

Makes 1 mL of composition: (2-Hydroxypropyl)-β-cyclodextrin (100 mg) was dissolved in water (527 µL). 5-FU solution (5-Fluorouracil Injection BP, 50 mg/mL, 300 µL) and 100 µL of folinic acid solution (Leucovorin Calcium 10 mg/mL) were added to the cyclodextrin solution which was agitated to mix. HCl (73 µL of 1.000 M solution) was added to the solution to bring the pH to 7.4±0.1. The solution was filtered under aseptic conditions and stored at room temperature, protected from light. This composition is named FD100HPc.

1.4 Preparation of a Composition from 5-Fluorouracil Solution (FD4 Method).

Makes 1 mL of composition: Heptakis(6-O-sulfo)-β-cyclodextrin sodium salt, (50 mg) was dissolved in water (527 µL). 5-FU solution (5-Fluorouracil Injection BP, 50 mg/mL, 300 µL) and 100 µL of folinic acid solution (Leucovorin Calcium 10 mg/mL) were added to the cyclodextrin solution which was agitated to mix. HCl (73 µL of 1.000 M solution) was added to the solution to bring the pH to 7.4±0.1. The solution was filtered under aseptic conditions and stored at room temperature, protected from light. This composition is named FD50-7Sc.

Example 2

Preliminary Stability Study of Compositions

A preliminary assessment of the stability of the compositions was carried out over a period of three weeks. Test samples were manufactured using the FD2 method described above and stored at room temperature. 5-FU is known to be light sensitive and therefore the samples were protected from exposure to light. The samples were monitored at set time intervals for signs of decomposition using a solution of the equivalent concentration of 5-FU in saline (0.9%) as a control. The methods of monitoring the solutions were physical appearance (solid formation etc.), pH and UV-VIS absorbance spectroscopy (266 nm). The 5-FU solution was warmed and sonicated to dissolve any solid 5-FU that had precipitated before pH and absorbance readings.

Figure 1:
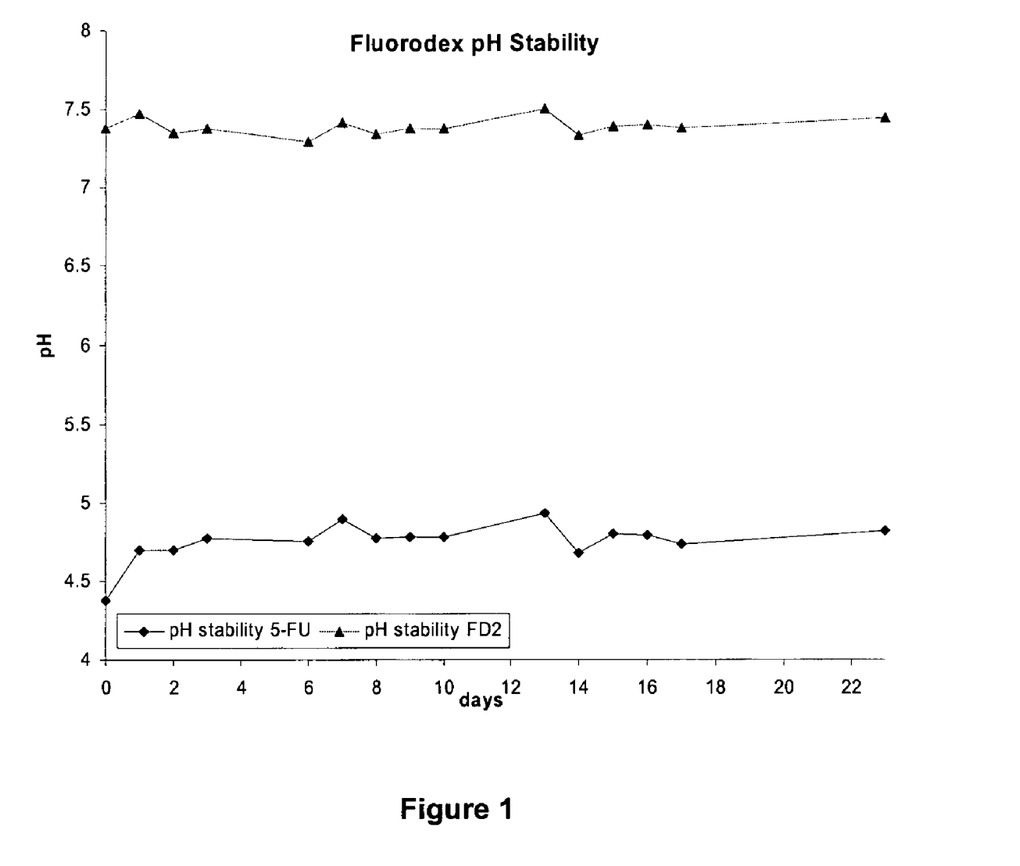
FIG. 1 shows the change in pH over time of a solution of the composition of the invention (denoted as FD2), and 5-FU.
Figure 2:
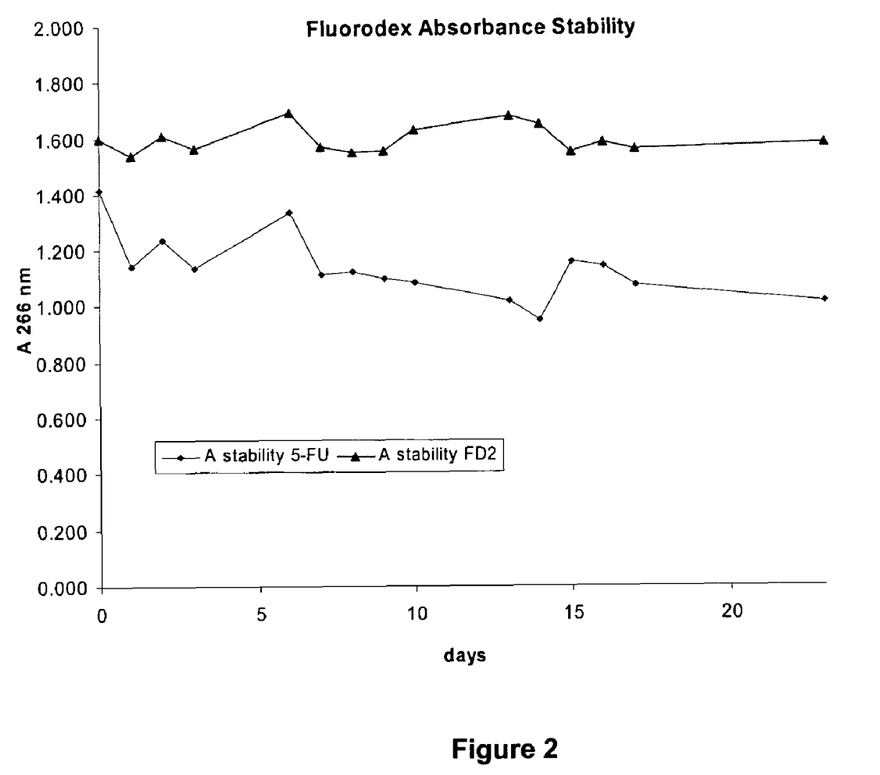
FIG. 2 shows the change in absorption at 266 nm of a solution of the composition of the invention (denoted as FD2), and 5-FU.

Results
1. No change was observed in the physical appearance of the composition, it remained a clear, almost colourless solution.
2. No significant change in pH over time was observed for the composition or 5-FU (see FIG. 1).
3. The samples for UV-VIS absorbance measurement were prepared by serial dilution from the test solutions. This may explain the minor deviations in the absorbance readings (FIG. 2). No overall trend of change in $A_{266}$ was observed over time for the composition or 5-FU.

Example 3

Compositions

Injectable Parenteral Composition

A pharmaceutical composition suitable for administration by injection may be prepared by mixing 1-5% by weight of the composition of the invention in 10% by volume propylene glycol and water. The solution is sterilised by filtration. The total amount of the composition may vary from patient to patient although a general dose might be about 750 mg of 5-FU, i.e. 50 mL of formulation that might be diluted with 5% glucose, 0.9% saline or sterile water to a volume of 100, 500, or 1000 mL.

Composition for Parenteral Administration

A composition for intramuscular injection could be prepared to contain 1 mL sterile buffered water, and 1 mL of the composition of the invention.

Similarly, a composition for intravenous infusion may comprise 250 ml of sterile Ringer's solution, and 5 mL of the composition of the invention.

Injectable Parenteral Composition

A composition suitable for administration by injection may be prepared by mixing 1% by weight of the composition of the invention by volume propylene glycol and water. The solution is sterilised by filtration.

Example 4

In Vitro Cytotoxicity

In vitro cytotoxicity assays were carried out on 5 different carcinoma cell lines (MDA-MB-231, HCT-116, COLO-201, PC-3 and PC-14) using 3 different compositions of the invention (FD45c, FD50-7Sc and FD100HPc). MDA-MB-231 is a breast cancer cell line, HCT-116 and COLO-201 are colon cancer cell lines, PC-3 is a prostate cancer cell line and PC-14 is a non-small cell lung cancer cell line.

Figure 3:
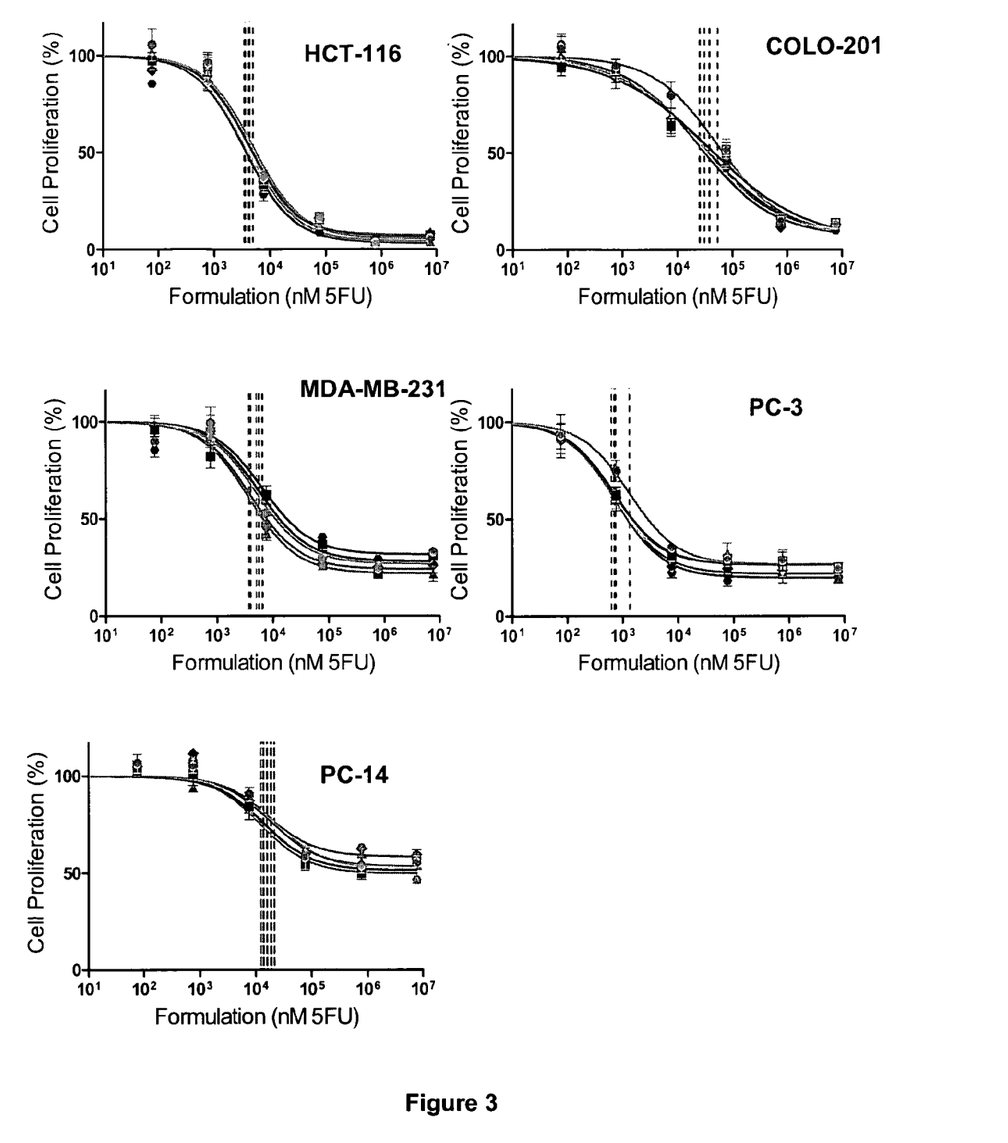
FIG. 3 shows dose-response curves for 5 carcinoma cell lines treated with increasing concentrations of various 5-FU formulations. After 72 h, cell proliferation was analysed by the MTS assay and normalised to saline control treatments (100% proliferation). ● 5-FU, ■ 5-FU:FA, ▲ FD45c, ◆ FD50-7Sc, ● FD100HPc. Dashed lines represent the $IC_{50}$ for each treatment (GraphPad). Values shown are mean±SD (n=4, except for HCT-116 FD50-7Sc and MDA-MB-231 FD100HPc where n=3)

The levels of 5-FU and FA remained constant in each composition. For comparison, assays were also performed using a combination of 5-FU and FA (5-FU:FA), and also 5-FU only. A summary of $IC_{50}$ values for all cell lines is presented in Table 1 below, and representative dose-response curves used to generate these $IC_{50}$ values are presented in FIG. 3. These results were analyzed by a 2-way ANOVA (GraphPad), which compared the effects of different cell lines and different treatments on $IC_{50}$ values.

Overall sensitivity to 5-FU was significantly different between cell lines (P<0.0001). PC-3 cells were the most sensitive, followed by HCT-116, MDA-MB-231, PC-14 and COLO-201 cells. Further, in COLO-201 and PC-14 cells, 5-FU was significantly less effective than 5-FU:FA (P=0.0084). Across all cell lines, each of compositions FD45c, FD50-7Sc and FD100HPc demonstrated in vitro cytotoxicity equivalent to 5-FU:FA (P>0.05 by Bonferroni post-tests comparing all treatments to 5-FU:FA, GraphPad).

TABLE 1

Summary of cytotoxicity results for various 5-FU treatments across 5 different carcinoma cell lines. Cell proliferation was analysed by the MTS assay and the concentration of 5-FU in each composition causing 50% of maximum growth inhibition was calculated ($IC_{50}$). Values shown are mean $IC_{50}$ ± SD, from at least 3 independent experiments across all cell lines and treatments.

| | $IC_{50}$ (μM 5-FU) | | | | |
|---|---|---|---|---|---|
| Cell Line | 5-FU | 5-FU:FA | FD45c | FD50-7Sc | FD100HPc |
| PC-3 | 1.4 ± 0.8 | 0.6 ± 0.4 | 0.8 ± 0.4 | 1.1 ± 0.8 | 0.6 ± 0.1 |
| HCT-116 | 4.0 ± 1.3 | 2.5 ± 1.3 | 3.4 ± 1.5 | 2.9 ± 1.1 | 2.0 ± 1.3 |
| MDA-MB-231 | 9.1 ± 1.4 | 9.1 ± 4.8 | 7.8 ± 2.3 | 9.6 ± 3.3 | 5.2 ± 1.5 |
| PC-14 | 33.4 ± 12.2 | 16.2 ± 12.5 | 17.3 ± 7.2 | 20.2 ± 7.4 | 20.3 ± 1.5 |
| COLO-201 | 39.3 ± 13.9 | 23.5 ± 11.1 | 20.8 ± 6.4 | 26.4 ± 6.3 | 26.8 ± 12.1 |

Example 5

In Vivo Single Dose Tolerance

Figure 4:
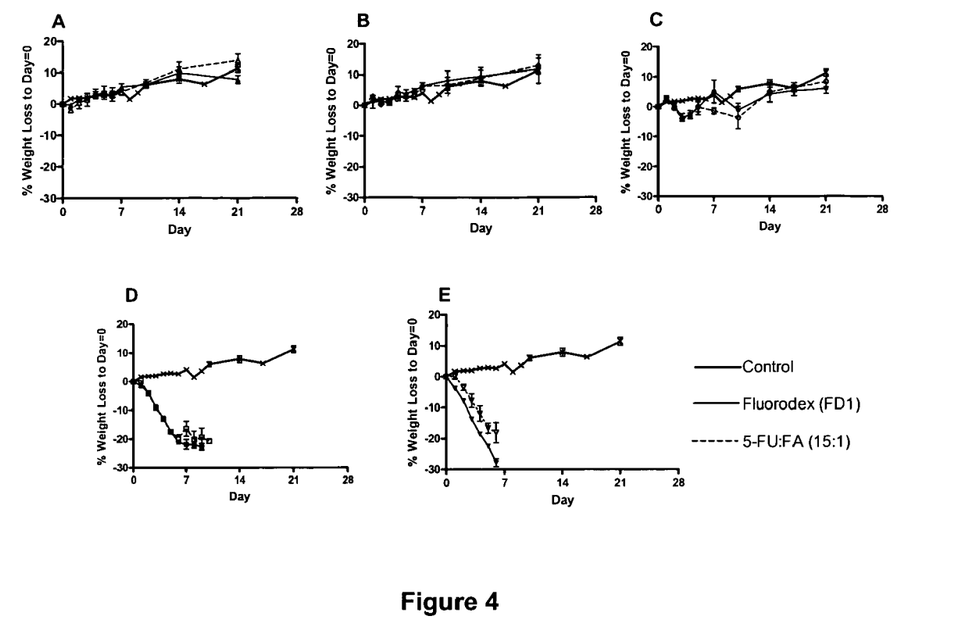
FIG. 4 depicts the single dose tolerance of a composition according to the present invention, compared to 5-FU:FA for Example 5, in which lines indicate mean±SEM, n=3: (A) 50 mg/kg; (B) 100 mg/kg; (C) 200 mg/kg; (D) 225 mg/kg and (E) 250 mg/kg.

In vitro assessment of a composition according to the present invention showed that it has similar $IC_{50}$ values to 5-FU, 5-FU:FA and 5-FU/β-CD against breast (MDA-MB-231) and colorectal (HCT-116) cells. Therefore in vivo toxicological assessment was undertaken. The dose tolerance of a composition according to the present invention which contains an equimass ratio of 5-FU to FA, was compared to that of 5-FU:FA and PBS control mice using a dose escalation protocol. Female Balb/c mice, 4-5 weeks of age were obtained from ARC (WA, Australia). Doses were administered by a single i.p. injection of not more than 200 µL. Animals were weighed for 5-days post treatment and then twice weekly until the end of the observation period (21-days post treatment). Endpoints were defined as a sustained 15% weight loss from day of treatment, or other signs of distress. FIG. 4 shows the single dose toxicity of the composition of the invention compared to 5-FU:FA.

Example 6

Fractionated Multiple Dose Tolerance

Figure 5:
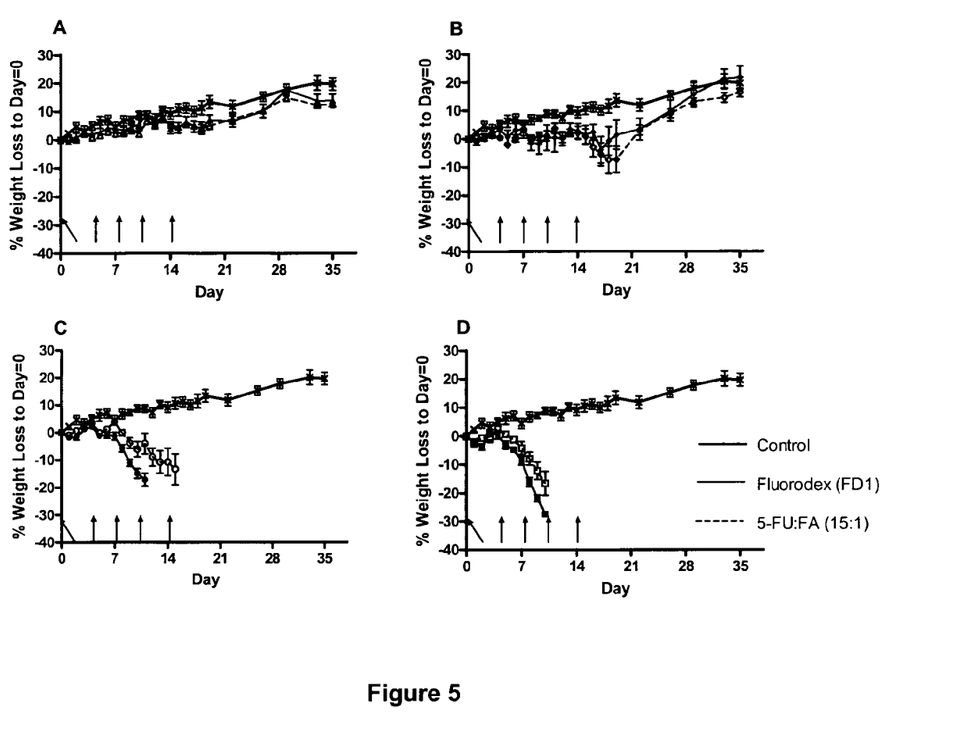
FIG. 5 shows fractionated multiple dose tolerance of FD1 compared to 5-FU:FA, for Example 6, in which lines indicate mean±SEM: (A) 20 mg/kg×5; (B) 40 mg/kg×5; (C) 60 mg/kg×5 and (D) 80 mg/kg×5.

The dose tolerance of a composition according to the present invention which contains an equimass ratio of 5-FU to FA, was compared to that of 5-FU:FA and PBS control mice using a dose escalation protocol. Female Balb/c mice, 4-5 weeks of age were obtained from ARC (WA, Australia). Doses were administered by an i.p. injection of not more than 200 µL. Five doses were administered over 14 days (indicated by arrows in FIG. 5). Animals were weighed daily during and 5-days post the last administration, and then twice weekly until the end of the observation period (21-days post the last treatment). Endpoints were defined as a sustained 15% weight loss from day of first treatment, or other signs of distress. Cohorts (n=6) were sacrificed when 2/6 mice reached these endpoints. FIG. 5 shows multiple dose toxicity of FD1 compared to 5-FU:FA.

Example 7

Efficacy I

Figure 6:
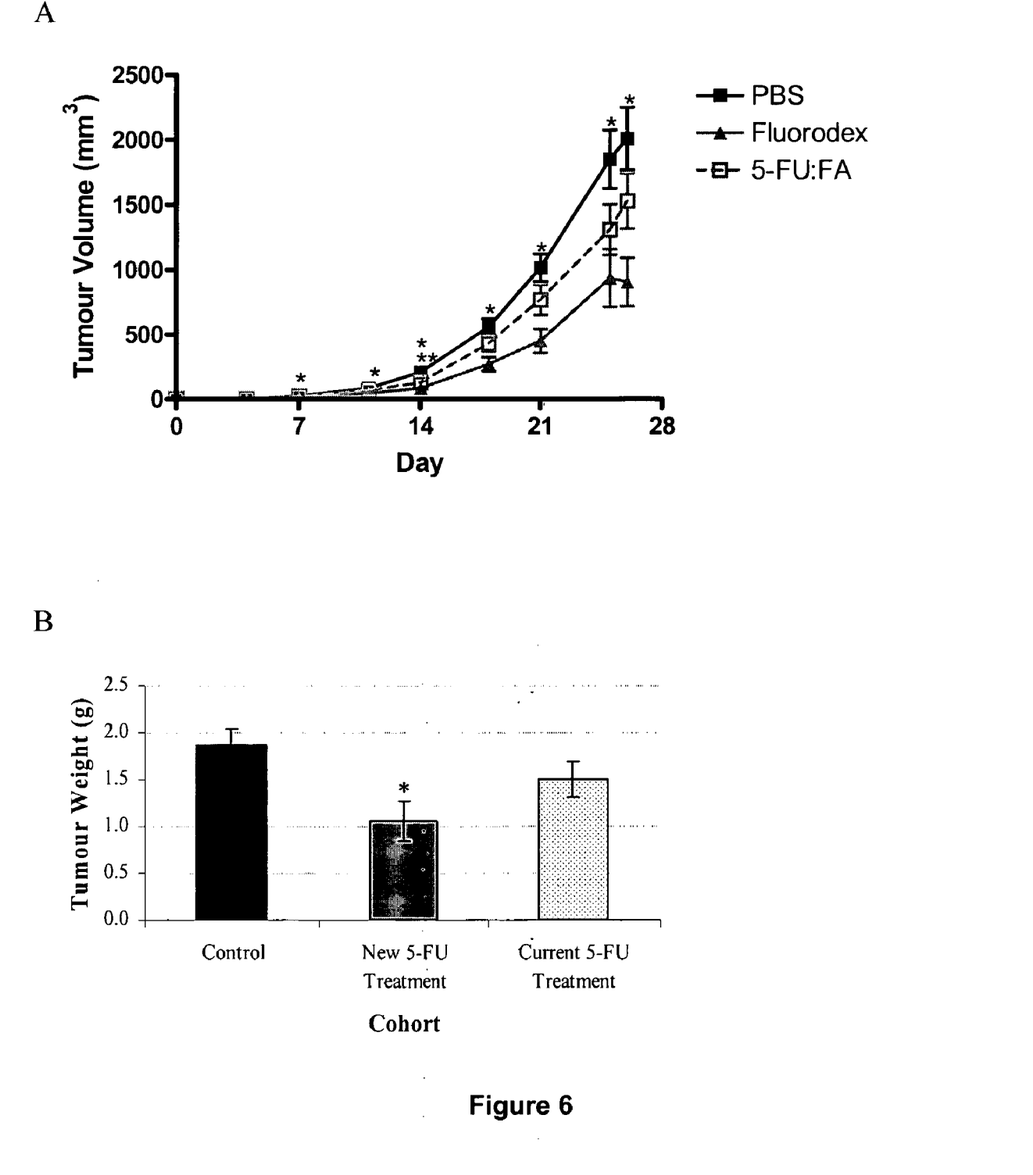
FIG. 6 depicts the efficacy of a composition according to the present invention compared to 5-FU:FA against MDA-MB-231 Xenografts for Example 7: (A) Tumor Growth—the dose response of a composition according to the present invention (FD2), which contains an equimolar amount of 5-FU to FA, was compared to that of 5-FU:FA and PBS (phosphate buffered saline); control mice: cohort sizes were n=10 and lines indicate mean±SEM, asterisks indicated significant differences to the control (p<0.05) (*) the composition according to the present invention, (**) 5-FU:FA; (B) Tumor Weight upon sacrifice-weight of tumor upon sacrifice: values indicate mean±SEM (standard error of mean), n=10, asterisks indicated significant differences to the control (p<0.05).

Female Balb/c nude mice were obtained from ARC (WA, Australia) aged 3-4 weeks. Mice were administered a single injection s.c. (approx 100 µL), containing 2 million MDA-MB-231 cells, into the mammary fat pad. Xenografts were allowed 10 days to establish after which time tumors were visible. Mice were then treated with a dose of 40 mg/kg×5 (within 14 days) by i.p. injection. For those in the 5-FU:FA cohort, mice were firstly administered the FA followed directly by the 5-FU injection. Mice tumors were measured externally using calipers and the tumor volume was determined by Vol=a×b²/2, where a is the largest and b is the smallest diameter respectively. Endpoints were defined as a tumor size for 15×15 mm, or that impeded movement, or a is sustained 15% weight loss or distressed behaviour. FIG. 6 shows the efficacy of a composition according to the present invention compared to 5-FU:FA against MDA-MB-231 Xenografts: (A) Tumor Growth The dose response of the composition of the invention (FD2), which contains an equimolar amount of 5-FU to FA, was compared to that of 5-FU:FA and PBS control mice Cohort sizes were n=10 and lines indicate mean±SEM. Asterisks indicated significant differences to the control (p<0.05) (*) the composition of the invention, (**) 5-FU:FA; (B) Tumor Weight upon sacrifice Weight of tumor upon sacrifice. Values indicate mean±SEM, n=10. Asterisks indicated significant differences to the control (p<0.05)

Example 8

Efficacy II

Breast tumours were induced by subcutaneous inoculation of 2 million MDA-MB-231 cells/site into mammary fat pads of 4-5 week old female athymic nude mice. Palpable tumours were observed at the majority of sites inoculated after 2 weeks. Three weeks after the breast cancer inoculation, the mice were administered a previously determined clinically relevant dose of the FD100HPc composition or 5-FU:FA in the absence of cyclodextrin. Each cohort size consisted of 10 animals to allow for statistical analysis. Each animal was routinely monitored with survival endpoints being defined as a sustained (>1, ≦3) 15% weight loss to Day 0, or distressed behaviour (e.g. lack of activity, no eating or drinking), or until tumour dimensions were >15 mm in diameter. The animals were not monitored for any longer than 3 months. The average tumour volume of mice who received the FD100HPC formulation was 750 $mm^3 \pm 72$ $mm^3$ (n=8) as compared to 830±101 $mm^3$ (n=9) in the mice who received 5-FU:FA in the absence of cyclodextrin. It was also noted that none of the cohort treatments caused a weight decline associated with cytotoxicity.

The invention claimed is:

1. A composition for treatment or delaying onset of cancer, said composition being a homogeneous composition comprising:
    (i) 5-fluorouracil (5-FU), or a pharmaceutically acceptable salt or analogue thereof;
    (ii) folinic acid, or a pharmaceutically acceptable salt thereof; and
    (iii) a cyclodextrin or a pharmaceutically acceptable salt or derivative thereof.

2. The composition of claim 1 wherein the pH of the composition is about 5 to about 9.

3. The composition of claim 1 wherein the cyclodextrin or salt or derivative thereof is present at a concentration of between about 10 and about 300 mg/ml.

4. The composition of claim 1 wherein the 5-FU or salt or analogue thereof is present at a concentration of between about 5 and about 50 mg/ml.

5. The composition of claim 1 wherein the folinic acid or salt thereof is present at a concentration of between about 1 and about 15 mg/ml.

6. The composition of claim 1 wherein the molar ratio of the cyclodextrin or pharmaceutically acceptable salt or derivative thereof to the 5-fluorouracil (5-FU), or pharmaceutically acceptable salt or analogue thereof is between about 1:10 and about 3:1.

7. The composition of claim 1 additionally comprising one or more pharmaceutically acceptable carrier, diluent and/or adjuvant.

8. The composition of claim 1 comprising an aqueous carrier.

9. The composition of claim 1, said composition being in the form of an aqueous solution.

10. The composition of claim 1 wherein the pharmaceutically acceptable salt of folinic acid is calcium folinate or sodium folinate.

11. The composition of claim 1 wherein the cyclodextrin is selected from the group consisting of: a hydroxyalkyl cyclodextrin, a sulfated cyclodextrin and a sulfoalkylether cyclodextrin, or a salt thereof.

12. The composition of claim 1 wherein the cyclodextrin is a β-cyclodextrin, or a salt thereof.

13. A process for making a composition for delaying onset and/or treatment of cancer, said process comprising combining:
    (i) 5-fluorouracil (5-FU), or a pharmaceutically acceptable salt or analogue thereof;
    (ii) folinic acid, or a pharmaceutically acceptable salt thereof; and (iii) a cyclodextrin or a pharmaceutically acceptable salt or derivative thereof.

14. The process of claim 13 comprising combining (i) with (iii), and then adding (ii).

15. The process of claim 14 wherein (ii) is added in aqueous solution.

16. The process of claim 14 wherein the step of combining (i) with (iii) is conducted in the presence of an aqueous solvent to form an aqueous solution.

17. The process of claim 13 additionally comprising sterilizing the composition.

18. A method for treatment or delaying onset of cancer in a patient in need of said treatment or delaying onset of cancer, said method comprising administration of a therapeutically effective amount of a composition according to claim 1.

19. The method of claim 18 wherein the cancer is selected from the group consisting of: prostate cancer, lung cancer, colo-rectal cancer, cervical cancer, breast cancer, ovarian cancer, gastric cancer, primary hepatoma, skin cancer, pancreatic cancer, cholangiocarcinoma and a cancer of the head or neck.

20. A method for inhibiting the proliferation of cancer cells, said method comprising exposing the cancer cells to a composition according to claim 1.

* * * * *